United States Patent [19]
Patt

[11] 3,946,599
[45] Mar. 30, 1976

[54] LIQUID APPLICATOR FOR ULTRA-SONIC TRANSDUCER

[76] Inventor: Jacob Patt, 22855 Essex Way, Southfield, Mich. 48075

[22] Filed: Nov. 8, 1974

[21] Appl. No.: 522,187

[52] U.S. Cl.............................. 73/71.5 US; 310/8.3
[51] Int. Cl.² ........................................ G01N 29/04
[58] Field of Search........ 73/71.5 U, 67.8 S, 67.8 R; 310/8.3, 8.7

[56] References Cited
UNITED STATES PATENTS

| | | | |
|---|---|---|---|
| 2,532,507 | 12/1950 | Meunier............................... | 310/8.7 |
| 3,584,327 | 6/1971 | Murry............................... | 310/8.7 X |

FOREIGN PATENTS OR APPLICATIONS

| | | | |
|---|---|---|---|
| 664,606 | 1/1952 | United Kingdom.............. | 73/71.5 U |

Primary Examiner—James J. Gill
Attorney, Agent, or Firm—Nathan Edelberg; Robert P. Gibson; Peter Taucher

[57] ABSTRACT

Attachments for an ultrasonic transducer used to measure discontinuities in a test specimen. The attachments constitute a series of liquid applicator heads selectively attachable to the transducer in accordance with differently contoured test specimens and specimen materials. Each applicator head is adapted to distribute a film of coupling liquid to the test specimen to improve energy transmission between the transducer and specimen.

The invention described herein may be manufactured, used, and licensed by or for the Government for governmental purposes without payment to me of any royalty thereon.

5 Claims, 4 Drawing Figures

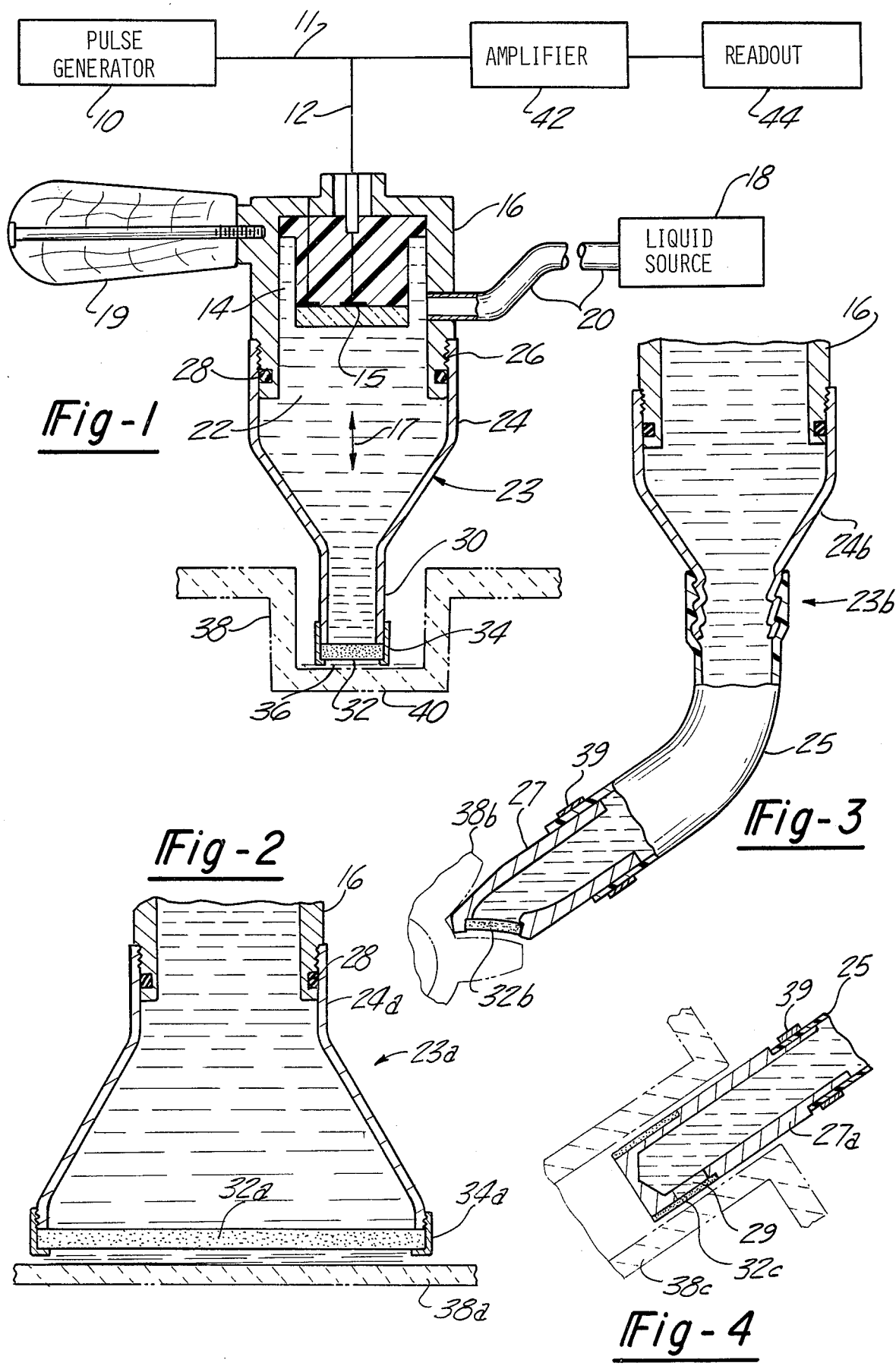

LIQUID APPLICATOR FOR ULTRA-SONIC TRANSDUCER

BACKGROUND AND SUMMARY OF INVENTION

The invention is an improvement on the invention disclosed in my U.S. Pat. application, Ser. No. 505,824, filed on Sept. 13, 1974. As there shown, an ultrasonic transducer is coupled to a test specimen by means of a liquid couplant supplied to the transducer from a remote source. The sensitivity of the apparatus is affected by the ability of the liquid couplant to transmit pulse energy between the specimen surface and oscillatable transducer element (piezo electric crystal or coil-diaphragm element). In the arrangement described in my aforesaid application Ser. No. 505,824, a coupling liquid is caused to continuously seep through a porous membrane locatable at the specimen surface, thereby forming a liquid film thereon; mechanical wave energy is transmitted to and/or from the specimen surface via the liquid film.

For best results the porous membrane should be sized and contoured so that it can take a position fairly close to the specimen surface; otherwise the liquid couplant will not effectively perform its energy-transmitting function. If the porous membrane has a relatively small exposed face area, it will accommodate itself to depressions or convex surfaces found on many test specimens (such as engine blocks, valve bodies, tire carcasses, gears, etc). However the membrane will then not be especially suited for scanning large surface areas such as are found on large sheets, vehicle hulls, etc.

The present invention proposes a transducer arrangement comprising a single transducer head and a plurality of different liquid applicator heads. Each applicator head is equipped with a porous membrane having a size and surface contour suited to scan a specific type of surface; e.g., a large flat surface or a small curved area (concave or convex.) The applicator heads are interchangeably usable with a single common transducer head. The invention enhances the usefulness of the transducer assembly while reducing its total cost.

THE DRAWINGS

FIG. 1 is a sectional view through a transducer assembly embodying the invention.

FIGS. 2 through 4 are fragmentary sectional views of different liquid applicator heads interchangeably usable in the FIG. 1 transducer assembly.

The transducer mechanism shown in FIG. 1 comprises a discontinuous voltage source 10 for generating time-spaced electrical pulses in electrical conductors 11 and 12. Conductor 12 delivers the pulses to a piezoelectric crystal 15 suitably mounted within a transducer housing 16; the crystal is constructed and mounted to oscillate in the vertical direction (denoted by numeral 17) when electrically excited by pulse generator 10.

A remote liquid source 18, preferably under positive pressure, is connected to a flexible liquid line 20 leading to a passage 22 formed within housing 16. A shut-off valve and/or pressure regulator valve (not shown) can be positioned in line 20 to provide desired flow conditions through passage 22. The flow is made sufficient to provide a liquid film on test specimen 38.

Transducer housing 16 has a detachable connection with any of several liquid applicator heads, including those shown in FIGS. 2 and 3. The applicator head 23 shown in FIG. 1 comprises a tubular section 24 having internal threads 26 adapted to rotatably engage mating threads on transducer housing 16; an O-ring 28 is provided on the housing for sealing the defined joint between the housing and applicator head. Other "quick disconnect" joints may be used between the housing and applicator head(s).

Applicator head 23 includes a small diameter tubular section 30 whose exit mouth is engaged with a porous membrane 32; an annular cap 34 may be screwed onto section 30 to retain membrane 32 in place. As explained in my aforementioned application, Ser. No. 505,824, the membrane functions as a flow controller to promote the formation of a continuous coupling film 36 on the surface of test specimen 38. The membrane openings are of sufficient size that the liquid quantities within the openings transmit wave energy substantially undampened by the membrane wall material; i.e., the wall material does not affect or influence the wave being transmitted by the liquid. The entire assembly, comprising housing 16 and applicator head 23, may be manually manipulated for scanning extended surface areas of the specimen, as by means of a handle 19 suitably attached to housing 16.

The transducer assembly can be used as a sender and/or receiver in various measuring techniques, as for example the "pulse-echo" technique. FIG. 1 illustrates the transducer assembly acting as a sender and a receiver in a pulse-echo arrangement. Electrical generator 10 electrically excites piezoelectric crystal 15 which mechanically excites the liquid couplant and the test specimen. Electric signals are delivered from generator 10 and crystal 15 through amplifier 42 to readout device 44.

The FIG. 1 transducer includes a liquid applicator head having a relatively small diameter liquid exit portion 30; this enables the head to be inserted into small clearance spaces on or adjacent to a test specimen. The small exposed surface area of membrane 32 is however disadvantageous when it becomes necessary to scan large surface areas of a specimen. For such large areas the larger applicator head shown in FIG. 2 is more desirable. The FIG. 2 head will screw on or otherwise connect with the FIG. 1 transducer as a replacement for the smaller FIG. 1 head; the screw-on portion of each head is the same diameter, the difference being in the transverse area at the exit-end of each head. The FIG. 2 applicator flares outwardly from its point of connection with the transducer housing, thereby providing a large area membrane 32a. In use, the FIG. 2 applicator head can be made to scan large surface areas more readily and more quickly than the FIG. 1 head. In some instances the smaller FIG. 1 head can be used to pinpoint the specimen internal discontinuities broadly identified by the FIG. 2 head.

FIG. 3 illustrates another liquid applicator 23b comprising a screw-on fitting or connector portion 24b and flexible conduit 25. An exit tube or fitting 27 is joined to the discharge end of conduit 25 to direct the coupling liquid through membrane 32b into contact with the surface of test specimen 38b; in this case the specimen is a gear. The transducer is suitable for detecting various defects in the gear teeth such as excessive porosity or inadequate case hardness depth.

Flexible conduit 25 may be of sufficient length to enable tube 27 to enter into the space required for investigation of the specimen. It is contemplated that transducer 16 be brought as close as possible to the specimen, and that conduit 25 be manipulated around any obstructions that might prevent straight line movement of tube 27 onto the specimen. A conduit 25 length of one or two feet is believed to be a practical compromise, providing suitable manipulation versatility without excessive pulse energy dissipation in the conduit 25 wall.

FIG. 4 fragmentarily illustrates a flexible conduit 25 fitted to a discharge tube 27a that is equipped with a liquid exit opening 29. A porous sleeve-type membrane 32c is telescoped onto tube 27a for liquid to act as a regulator for liquid flowing out through opening 29. The FIG. 4 applicator is adapted for use with tube-like specimens 38c. During such use tube 27a may be moved axially along the specimen surface and also rotatably therearound to scan the specimen surface area.

In general, it is contemplated that various differently sized and differently configured applicators will be interchangeably used with a single transducer head to facilitate the scanning of various specimen surfaces, such as grooves, holes, flats, ridges, etc. Applicators employing flexible conduits 25 may be used when it is otherwise impractical to bring the transducer into sufficient proximity to the specimen surface.

Preferably the liquid applicators are designed so that each porous membrane is readily cleanable, as for example after the tester has been in prolonged use. A screw-on cap 34 or 34a (or other quick disconnect cap structure) is used as a membrane retention device thereby enabling the cap to be removed for membrane-cleaning purposes. In the case of the applicators shown in FIGS. 3 and 4 tube 27 or 27a may be removed from conduit 27 to facilitate cleaning of the membrane; the components are in this case releasably connected together by a conventional hose-clamp 39 or equivalent device.

I wish it to be understood that I do not desire to be limited to the exact details of construction shown and described, for obvious modifications will occur to a person skilled in the art.

I claim:

1. In an ultrasonic transducer assembly for locating variations and discontinuities in a test specimen comprising an electro-mechanical transducer head that includes an oscillatable element, passage means for locating a coupling liquid in energy-transmitting relation to the oscillatable element, and liquid source means for replenishing liquid that flows through the passage means: the improvement comprising a number of liquid applicators individually connectable to the passage means to apply the coupling liquid to the test specimen surface; each applicator being detachable from the passage means to permit interchangeable use of differently configured applicators with a single transducer head; each applicator comprising a liquid entrance fitting detachably connectable to the transducer passage means, a liquid exit mouth remote from the entrance fitting, and a conduit interconnecting the entrance fitting and exit mouth; one of said applicators having an exit mouth that has a relatively small transverse area for traversing small specimen surfaces.

2. The transducer assembly of claim 1: wherein the conduit in at least one of the applicators is formed of a flexible material.

3. The transducer assembly of claim 2: the flexible conduit having a sufficient length to permit manipulation of the applicator around obstructions in the vicinity of the specimen surface.

4. The transducer assembly of claim 1: each applicator including a porous wall located at its exit mouth for controlling outflow therethrough, the openings in said wall being sized so that liquid within the openings transmits wave energy substantially undampened by the wall material; said porous wall having an outer surface conforming to the contour of the specimen surface under test.

5. The transducer assembly of claim 4: at least one of the applicators including a conduit that has an appreciable length, whereby the transducer head is locatable remote from the specimen surface.

* * * * *